US011801355B2

(12) United States Patent
Zorzi de Miranda et al.

(10) Patent No.: US 11,801,355 B2
(45) Date of Patent: Oct. 31, 2023

(54) OXYGEN TANK DURATION OF USE

(71) Applicant: KYNDRYL, INC., New York, NY (US)

(72) Inventors: Isabel Carolina Zorzi de Miranda, Sao Paulo (BR); Sergio Varga, Campinas (BR); Claudio Keiji Iwata, Sao Paulo (BR); Marcia Ito, Sao Paulo (BR); Maria Clara Verçosa Da Silva Rodrigues, Rio de Janeiro (BR)

(73) Assignee: Kyndryl, Inc., New York, NY (US)

( * ) Notice: Subject to any disclaimer, the term of this patent is extended or adjusted under 35 U.S.C. 154(b) by 462 days.

(21) Appl. No.: 16/953,532

(22) Filed: Nov. 20, 2020

(65) Prior Publication Data
US 2022/0160976 A1 May 26, 2022

(51) Int. Cl.
*G08B 21/00* (2006.01)
*A61M 16/00* (2006.01)
(Continued)

(52) U.S. Cl.
CPC .... *A61M 16/0003* (2014.02); *A61M 16/1005* (2014.02); *F17C 13/02* (2013.01);
(Continued)

(58) Field of Classification Search
CPC .......... A61M 16/0003; A61M 16/1005; A61M 2016/0027; A61M 2202/0208; A61M 2205/3386; A61M 2205/3306; A61M 2205/3313; A61M 2205/332; A61M 2205/3331; A61M 2205/3368; A61M 2205/3375; A61M 2205/3553; A61M 2205/3592; A61M 2205/50; A61M 2205/505; A61M 2230/06; A61M 2230/205; A61M 2230/30; A61M 2230/63; F17C 13/02; F17C 2270/02; G16H 20/13;
(Continued)

(56) References Cited

U.S. PATENT DOCUMENTS 9,375,142 B2 6/2016 Schultz
9,581,539 B2 2/2017 Brugnoli
(Continued)

FOREIGN PATENT DOCUMENTS

CN 202568219 U 12/2012
CN 206813270 U 12/2017
(Continued)

OTHER PUBLICATIONS

Mell et al., "The NIST Definition of Cloud Computing", National Institute of Standards and Technology, Special Publication 800-145, Sep. 2011, pp. 1-7.
(Continued)

*Primary Examiner* — Mark S Rushing
(74) *Attorney, Agent, or Firm* — Zilka-Kotab, P.C.

(57) ABSTRACT

The exemplary embodiments disclose a method, a computer program product, and a computer system for determining a duration of use left in an oxygen tank. The exemplary embodiments may include collecting data of a user and corresponding oxygen tank, extracting one or more features from the collected data, and determining a duration of use left in the oxygen tank based on the extracted one or more features and one or more models.

20 Claims, 5 Drawing Sheets

(51) Int. Cl.
  G16H 40/40  (2018.01)
  G16H 40/67  (2018.01)
  G16H 20/13  (2018.01)
  G16H 20/30  (2018.01)
  F17C 13/02  (2006.01)
  A61M 16/10  (2006.01)

(52) U.S. Cl.
  CPC ............ *G16H 20/13* (2018.01); *G16H 20/30* (2018.01); *G16H 40/40* (2018.01); *G16H 40/67* (2018.01); *A61M 2016/0027* (2013.01); *A61M 2202/0208* (2013.01); *A61M 2205/3386* (2013.01); *F17C 2270/02* (2013.01)

(58) Field of Classification Search
  CPC ........ G16H 20/30; G16H 40/40; G16H 40/67; G16H 40/63
  USPC ........................................................ 340/632
  See application file for complete search history.

(56) References Cited

U.S. PATENT DOCUMENTS

| | | | | |
|---|---|---|---|---|
| 10,358,199 | B1* | 7/2019 | Kleinigger | B63C 11/26 |
| 11,168,840 | B1* | 11/2021 | Dean | G01F 1/56 |
| 2003/0032871 | A1* | 2/2003 | Selker | G16H 50/50 |
| | | | | 600/301 |
| 2008/0251074 | A1 | 10/2008 | Sand | |
| 2016/0346614 | A1* | 12/2016 | Kirby | G16H 40/63 |
| 2019/0212323 | A1* | 7/2019 | Gupta | G16C 20/20 |
| 2020/0289784 | A1* | 9/2020 | Commerford | A61M 16/1005 |
| 2021/0046265 | A1* | 2/2021 | Obenchain | A61M 16/0666 |
| 2022/0076822 | A1* | 3/2022 | Liu | G06F 21/31 |

FOREIGN PATENT DOCUMENTS

| | | |
|---|---|---|
| CN | 108472464 A | 8/2018 |
| GB | 2404593 A | 8/2003 |
| WO | 2009036327 A1 | 3/2009 |
| WO | 201914356 A2 | 7/2019 |

OTHER PUBLICATIONS

American Lung Association, "Our Vision is a World Free of Lung Disease", https://www.lung.org/?gclid=EAlaIQobChMI1dPh29Ob7QIVjJ6zCh1d . . . , printed Nov. 24, 2020, pp. 1-7.

Chouvarda et al, "WELCOME—Innovative Integrated Care platform using Wearable Sensing and Smart Cloud Computing for COPD patients with Comorbidities", 2014 IEEE, pp. 3180-3183.

Disclosed Anonymously, "An Adaptive Medical Oxygen Flow System", IP.com No. IPCOM00025900D, Aug. 15, 2019, pp. 1-4.

Edwards, "All About Manometers—What They Are and How They Work", https://www.thomasnet.com/articles/instruments-controls/all-about-man . . . ,printed Jun. 1, 2020, pp. 1-4.

Garth, "How Do Dive Computers Work?", https://beachbaby.net/how-do-dive-computers-work/, Oct. 16, 2016, pp. 1-8.

Ghazal et al., "Using machine learning models to predict oxygen saturation following ventilator support adjustment in critically ill children: A single center pilot study", PLos One, 2019, 14 (2): e0198921, pp. 1-16.

Grandview Research, Oxygen Therapy Market Size, share and Trends Analysis Report by Product (Oxygen Source Equipment, Oxygen Delivery Devices, Static, Dynamic), by application, By End-User, and Segment Forecasts, 2018-2024, Report ID: 978 1-68038-829-9, https://www.grandviewresearch.com/industry-analysis/oxygen-therapy- . . . , Mar. 2018, pp. 1-125.

IBM, "Watson Health: Get the Facts", https://www.ibm.com/watson-health/about/get-the-facts, printed Nov. 24, 2020, pp. 1-7.

World Health Organization, "Global Surveillance, prevention and control of Chronic Respiratory Diseases", A comprehensive approach, ISBN 978 92 4 156346 8, 2007, http://www.who.int/gard/publications/GARD%20Book%202007.pdf?, pp. 1-155.

Youtube, "UltraMaxO2 Oxygen Analyzer", https://www.youtube.com/watch?v=KxVClbpnqkU, Aug. 19, 2019, pp. 1-2.

* cited by examiner

OXYGEN TANK DURATION OF USE

BACKGROUND

The exemplary embodiments relate generally to oxygen tanks, and more particularly to the duration of use left in oxygen tanks.

Many people use oxygen therapy as a treatment for various medical conditions. Many people using oxygen therapy are not aware of how much time they have left to breathe oxygen from their current oxygen tank. As a result, they may experience anxiety and stress, and may experience life risks in the event of their oxygen tank running out of oxygen. For example, a patient may leave their home to buy groceries without being aware that their oxygen tank will run out of oxygen in ten minutes and may experience life risks as a result of their oxygen tank running out of oxygen while out at a grocery store.

SUMMARY

The exemplary embodiments disclose a method, a computer program product, and a computer system for determining a duration of use left in an oxygen tank. The exemplary embodiments may include collecting data of a user and corresponding oxygen tank, extracting one or more features from the collected data, and determining a duration of use left in the oxygen tank based on the extracted one or more features and one or more models.

BRIEF DESCRIPTION OF THE SEVERAL VIEWS OF THE DRAWINGS

The following detailed description, given by way of example and not intended to limit the exemplary embodiments solely thereto, will best be appreciated in conjunction with the accompanying drawings, in which.

The drawings are not necessarily to scale. The drawings are merely schematic representations, not intended to portray specific parameters of the exemplary embodiments. The drawings are intended to depict only typical exemplary embodiments. In the drawings, like numbering represents like elements.

DETAILED DESCRIPTION OF THE SEVERAL VIEWS OF THE DRAWINGS

Figure 1:
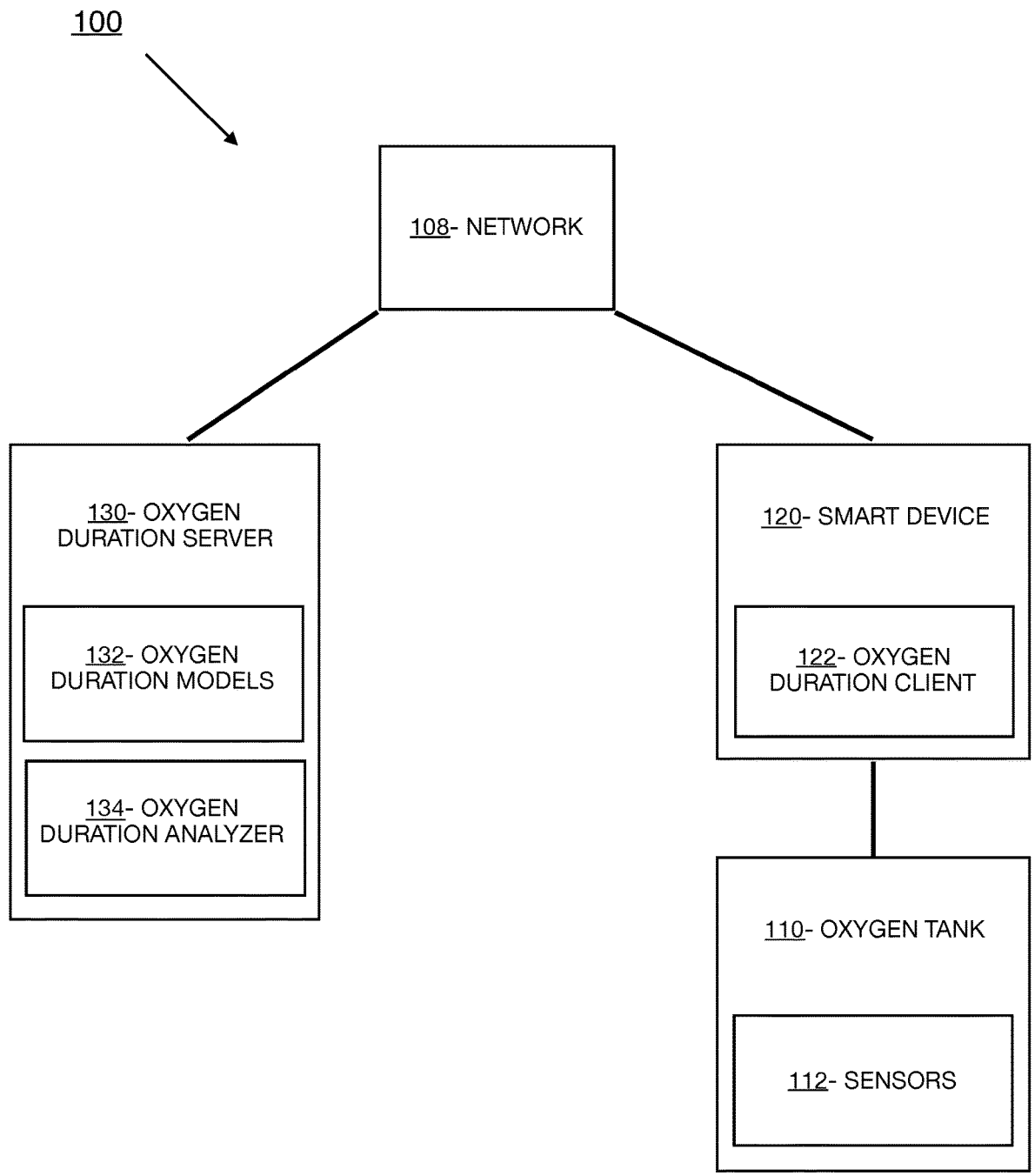
FIG. 1 depicts an exemplary schematic diagram of an oxygen duration system 100, in accordance with the exemplary embodiments.

Detailed embodiments of the claimed structures and methods are disclosed herein; however, it can be understood that the disclosed embodiments are merely illustrative of the claimed structures and methods that may be embodied in various forms. The exemplary embodiments are only illustrative and may, however, be embodied in many different forms and should not be construed as limited to the exemplary embodiments set forth herein. Rather, these exemplary embodiments are provided so that this disclosure will be thorough and complete, and will fully convey the scope to be covered by the exemplary embodiments to those skilled in the art. In the description, details of well-known features and techniques may be omitted to avoid unnecessarily obscuring the presented embodiments.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described.

In the interest of not obscuring the presentation of the exemplary embodiments, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is focused on the distinctive features or elements according to the various exemplary embodiments.

Many people use oxygen therapy as a treatment for various medical conditions. Many people using oxygen therapy are not aware of how much time they have left to breathe oxygen from their current oxygen tank. As a result, they may experience anxiety and stress, and may experience life risks in the event of their oxygen tank running out of oxygen. For example, a patient may leave their home to buy groceries without being aware that their oxygen tank will run out of oxygen in ten minutes and may experience life risks as a result of their oxygen tank running out of oxygen while out at a grocery store.

Exemplary embodiments are directed to a method, computer program product, and computer system for determining a duration of use left in an oxygen tank 110. In embodiments, machine learning may be used to create models capable of determining a duration of use left in an oxygen tank 110, while feedback loops may improve upon such models. Moreover, data from user uploads, databases, or the sensors 112 may be used to determine a duration of use left in an oxygen tank 110. A user may wish to know a duration of use left in their oxygen tank 110 for a number of purposes or circumstances. For example, a user may wish to know the duration of use left in their oxygen tank 110 before departing on a vacation or before leaving their house to run errands such that they are able to avoid their oxygen tank 110 running out of oxygen while away from home. In another example, a user staying at home may still wish to know the duration of use left in their oxygen tank 110 so that they can purchase a replacement oxygen tank 110 in anticipation of their current oxygen tank 110 running out of oxygen. In general, it will be appreciated that embodiments described herein may relate to determining a duration of use left in an oxygen tank 110 within any environment and for any motivation.

FIG. 1 depicts the oxygen duration system 100, in accordance with the exemplary embodiments. According to the exemplary embodiments, the oxygen duration system 100 may include an oxygen tank 110, smart device 120, and an oxygen duration server 130, which may be interconnected via a network 108. While programming and data of the exemplary embodiments may be stored and accessed remotely across several servers via the network 108, programming and data of the exemplary embodiments may alternatively or additionally be stored locally on as few as one physical computing device or amongst other computing devices than those depicted.

In the exemplary embodiments, the network 108 may be a communication channel capable of transferring data between connected devices. Accordingly, the components of the oxygen duration system 100 may represent network components or network devices interconnected via the network 108. In the exemplary embodiments, the network 108 may be the Internet, representing a worldwide collection of networks and gateways to support communications between devices connected to the Internet. Moreover, the network 108 may utilize various types of connections such as wired, wireless, fiber optic, etc. which may be implemented as an intranet network, a local area network (LAN), a wide area network (WAN), or a combination thereof. In further embodiments, the network 108 may be a Bluetooth network, a Wi-Fi network, or a combination thereof. In yet further embodiments, the network 108 may be a telecommunications network used to facilitate telephone calls between two or more parties comprising a landline network, a wireless network, a closed network, a satellite network, or a combination thereof. In general, the network 108 may represent any combination of connections and protocols that will support communications between connected devices.

In the example embodiment, the oxygen tank 110 includes one or more sensors 112, and may be any kind, shape, size, etc. of tank that may contain oxygen. In embodiments, the oxygen tank 110 may be a smart oxygen tank 110 that may include an enterprise server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, an IoT device, or any other electronic device or computing system capable of receiving and sending data to and from other computing devices. While the oxygen tank 110 is shown as a single device, in other embodiments, the oxygen tank 110 may be comprised of a cluster or plurality of computing devices, in a modular manner, etc., working together or working independently.

In example embodiments, the sensors 112 may comprise a camera, microphone, heart rate sensor, blood pressure sensor, oximeter sensor, manometer sensor, movement detection sensor, pressure detection sensor, thermometer, speedometer, accelerometer, gyroscope, light sensor, infrared sensor, smell sensor, or other sensory hardware equipment. Moreover, the oxygen tank 110 may incorporate an array of the one or more sensors 112 such that information can be obtained by the sensors 112 in multiple directions, at different times/intervals, in different mediums/frequencies, and the like. For example, the oxygen tank 110 may include three forward-facing cameras that each record an adjacent sixty-degree viewing angle spanning a total of one-hundred and eighty degrees in the direction of a user. Moreover, data processing techniques may be implemented such that directional information of visual and audio data can be obtained based on signals received by each of the three sensors 112, such as trilateration and triangulation.

While the sensors 112 are depicted as integrated with the oxygen tank 110, in embodiments, the sensors 112 may be incorporated within an environment in which the oxygen duration system 100 is implemented. For example, the sensors 112 may be one or more microphones built into an auditorium, a camera built into a facility, a heart rate sensor, blood pressure sensor, oximeter sensor, manometer sensor, etc. Moreover, data processing techniques may be implemented such that directional information of visual and audio data can be obtained based on signals received by each of the sensors 112, such as trilateration and triangulation. In other embodiments, the sensors 112 may be integrated with other smart devices, e.g., smart phones and laptops, within an environment implementing the oxygen duration system 100. In such embodiments, the sensors 112 may communicate directly with other networks and devices, such as the network 108. The sensors 112 are described in greater detail as a hardware implementation with reference to FIG. 3, as part of a cloud implementation with reference to FIG. 4, and/or as utilizing functional abstraction layers for processing with reference to FIG. 5.

In the example embodiment, the smart device 120 includes an oxygen duration client 122, and may be an enterprise server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, an IoT device, or any other electronic device or computing system capable of receiving and sending data to and from other computing devices. While the smart device 120 is shown as a single device, in other embodiments, the smart device 120 may be comprised of a cluster or plurality of computing devices, in a modular manner, etc., working together or working independently. The smart device 120 is described in greater detail as a hardware implementation with reference to FIG. 3, as part of a cloud implementation with reference to FIG. 4, and/or as utilizing functional abstraction layers for processing with reference to FIG. 5.

The oxygen duration client 122 may act as a client in a client-server relationship with a server, for example an oxygen duration server 130. The oxygen duration client 122 may also be a software and/or hardware application capable of communicating with and providing a user interface for a user to interact with a server via the network 108. Moreover, in the example embodiment, the oxygen duration client 122 may be capable of transferring data from the sensors 112 between the oxygen tank 110, smart device 120, oxygen duration server 130, and other devices via the network 108. In embodiments, the oxygen duration client 122 utilizes various wired and wireless connection protocols for data transmission and exchange, including Bluetooth, 2.4 gHz and 5 gHz internet, near-field communication, Z-Wave, Zigbee, etc. The oxygen duration client 122 is described in greater detail with respect to FIG. 2.

In the exemplary embodiments, the oxygen duration server 130 may include one or more oxygen duration models 132 and an oxygen duration analyzer 134, and may act as a server in a client-server relationship with the oxygen duration client 122. The oxygen duration server 130 may be an enterprise server, a laptop computer, a notebook, a tablet computer, a netbook computer, a PC, a desktop computer, a server, a PDA, a rotary phone, a touchtone phone, a smart phone, a mobile phone, a virtual device, a thin client, an IoT device, or any other electronic device or computing system capable of receiving and sending data to and from other computing devices. While the oxygen duration server 130 is shown as a single device, in other embodiments, the oxygen duration server 130 may be comprised of a cluster or plurality of computing devices, working together or working independently. The oxygen duration server 130 is described in greater detail as a hardware implementation with reference to FIG. 3, as part of a cloud implementation with reference to FIG. 4, and/or as utilizing functional abstraction layers for processing with reference to FIG. 5.

The oxygen duration models 132 may be one or more algorithms modelling a correlation between one or more features detected by the sensors 112 and a duration of use left in an oxygen tank 110. In the example embodiment, the oxygen duration models 132 may be generated using machine learning methods, such as neural networks, deep learning, hierarchical learning, Gaussian Mixture modelling, Hidden Markov modelling, and K-Means, K-Medoids, or Fuzzy C-Means learning, etc., and may model a likelihood of one or more features being indicative of a duration of use left in an oxygen tank 110. In embodiments, such features may include user features such as age, heart rate, blood pressure, blood oxygen level, nervousness, pain, depression, hunger, sweating, etc. The oxygen duration models 132 may further include tank usage features such as tank size, tank oxygen capacity, oxygen purity, date/time of tank changes, breaks in usage, weather, seasons, locations, etc. The oxygen duration models 132 may weight the features based on an effect that the features have on determining a duration of use left in an oxygen tank 110.

In the exemplary embodiments, the oxygen duration analyzer 134 may be a software and/or hardware program capable of collecting training data, extracting features from the training data, and training one or more models based on the extracted features. The oxygen duration analyzer 134 may additionally be capable of configuring a session and collecting data, extracting features from the collected data, and applying one or more models to the extracted features to determine a duration of use left in an oxygen tank 110. Moreover, the oxygen duration analyzer 134 may be further configured for notifying the user and other people of the duration of use left in an oxygen tank 110. The oxygen duration analyzer 134 is additionally capable of evaluating whether the duration of use left in the oxygen tank 110 was determined appropriately and adjusting the one or more models. The oxygen duration analyzer 134 is described in greater detail with reference to FIG. 2.

Figure 2:
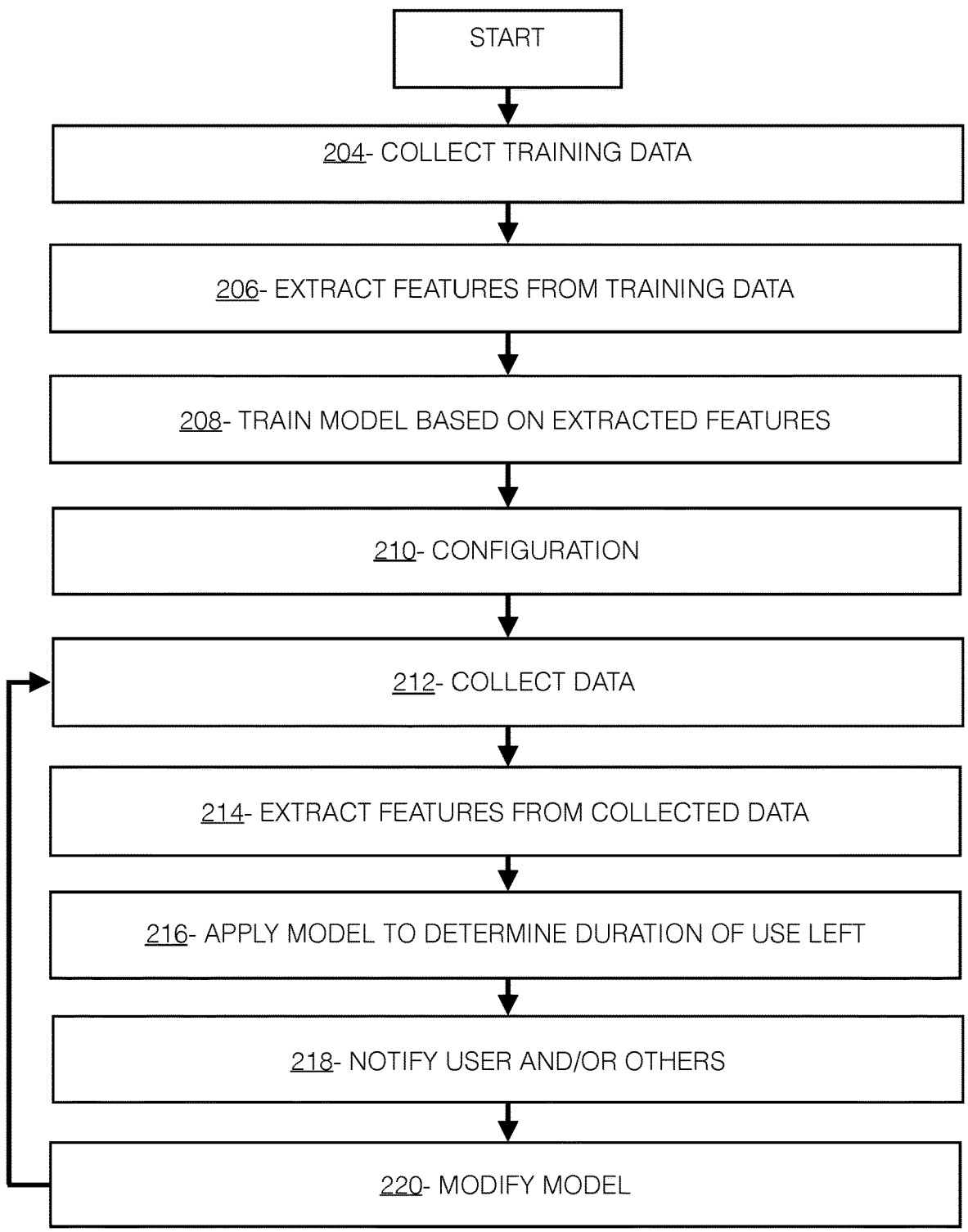
FIG. 2 depicts an exemplary flowchart illustrating the operations of an oxygen duration analyzer 134 of the oxygen duration system 100 in determining a duration of use left in an oxygen tank 110, in accordance with the exemplary embodiments.

FIG. 2 depicts an exemplary flowchart illustrating the operations of an oxygen duration analyzer 134 of the oxygen duration system 100 in determining a duration of use left in an oxygen tank 110, in accordance with the exemplary embodiments. In exemplary embodiments, the oxygen duration analyzer 134 first implements a training phase in which it trains the oxygen duration models 132 using training data including data of various users, data of various oxygen tanks 110 and usage conditions, and associated durations of use left in the oxygen tanks 110. In embodiments, the oxygen duration analyzer 134 may utilize the trained oxygen duration models 132 to determine a duration of use left in an oxygen tank 110. The oxygen duration analyzer 134 then moves on to an operational phase in which it applies the trained oxygen duration models 132 to a current user's usage of an oxygen tank 110 in order to determine a duration of use left in the user's oxygen tank 110.

The oxygen duration analyzer 134 may collect and/or receive training data (step 204). In embodiments, training data may include data of various users, data of various oxygen tanks 110 and usage conditions, and associated durations of use left in the oxygen tanks 110. The oxygen duration analyzer 134 may retrieve training data via user upload/input, databases, or the sensors 112. In embodiments, the oxygen duration analyzer 134 may collect training data via the sensors 112 as one or more microphones built into an auditorium, a camera built into a facility, a global positioning services (GPS) sensor worn by a user, a heart rate monitor worn by a user, an oximeter sensor measuring oxygen levels of a user's blood, of the user's oxygen tank 110, of the air around the user, etc. For example, heart rate monitor and blood pressure sensors 112 may collect a user's heart rate and blood pressure. The training data may additionally include user input specifying that the user was stressed and hungry while using their oxygen tank 110. The collected data may be associated with a tank oxygen capacity and duration of use left in the oxygen tank 110. The collected data may additionally comprise GPS data to determine a user's location and/or activity. For example, GPS data that indicates that the user is at their home may be correlated to a lower oxygen consumption rate, while GPS data that indicates that the user is at a gym may be correlated to a higher oxygen consumption rate. In embodiments, collected training data may also be associated to one or more users. For example, data of John's heart rate and blood pressure may be labelled with, "user: John." The oxygen duration analyzer 134 may collect training data associated with specific users to later train different oxygen duration models 132 for different users based on the users' preferences, characteristics, and/or tendencies. In embodiments, the oxygen duration analyzer 134 may collect training data to train one oxygen duration model 132 to determine a duration of use left in an oxygen tank 110 for all users.

To further illustrate the operations of the oxygen duration analyzer 134, reference is now made to an illustrative example where the oxygen duration analyzer 134 collects training data consisting of data of various users, data of various oxygen tanks 110 and usage conditions, and associated durations of use left in the oxygen tanks 110.

The oxygen duration analyzer 134 may extract one or more features from the collected and/or received training data (step 206). The extracted features may be extracted from the collected training data, which may include data collected via user upload/input, databases, or the sensors 112, etc. of one or more users and/or one or more usage conditions of one or more oxygen tanks 110. The extracted features may include user features such as age, heart rate, blood pressure, blood oxygen level, nervousness, pain, depression, hunger, sweating, etc. The extracted features may further include tank usage features such as tank size, tank oxygen capacity, oxygen purity, date/time of tank changes, breaks in usage, weather, seasons, locations, etc. In embodiments, the oxygen duration analyzer 134 may use techniques such as feature extraction, natural language processing, sentiment analysis, optical character recognition, image processing, audio processing, pattern/template matching, data comparison, etc. to identify user features such as age, heart rate, blood pressure, blood oxygen level, nervousness, pain, depression, hunger, sweating, etc. For example, the oxygen duration analyzer 134 may extract an age, weight, height, etc. directly from one or more databases via optical character recognition, a heart rate, blood pressure, blood oxygen level, etc. directly from one or more sensors 112 via natural language processing, and nervousness, pain, depression, hunger, sweating, etc. from user upload/input, sentiment analysis, image processing, etc. In embodiments, the oxygen duration analyzer 134 may extract user features such as age, heart rate, blood pressure, blood oxygen level, nervousness, pain, depression, hunger, sweating, etc.

In addition to extracting user features such as age, heart rate, blood pressure, blood oxygen level, nervousness, pain, depression, hunger, sweating, etc., the oxygen duration analyzer 134 may also extract tank usage features such as tank size, tank oxygen capacity, oxygen purity, date/time of tank changes, breaks in usage, weather, seasons, locations, etc. (step 206 continued). In embodiments, the oxygen duration analyzer 134 may use techniques such as feature extraction, image/video processing, timestamp analysis, pattern/template matching, data comparison, convolutional neural networks, etc. to identify tank usage features such as tank size, tank oxygen capacity, oxygen purity, date/time of tank changes, breaks in usage, weather, seasons, locations, etc. For example, the oxygen duration analyzer 134 may extract a tank size and tank oxygen capacity directly from one or more databases or user upload/input via optical character recognition, date and/or time of tank changes, breaks in usage, weather, seasons, locations, etc. directly from GPS data of the sensors 112, video collected by the sensors 112 via image/video processing, timestamp analysis, oxygen purity of an oxygen tank 110 directly from an oximeter sensor measurement, etc. The oxygen duration analyzer 134 may later associate extracted features with the duration of use left in one or more oxygen tanks 110 when training one or more models.

With reference to the previously introduced example where the oxygen duration analyzer 134 collects training data consisting of data of various users, data of various oxygen tanks 110 and usage conditions, and associated durations of use left in the oxygen tanks 110, the oxygen duration analyzer 134 extracts user features such as age, heart rate, blood pressure, blood oxygen level, nervousness, pain, depression, hunger, sweating, etc. as well as tank usage features such as tank size, tank oxygen capacity, oxygen purity, date/time of tank changes, breaks in usage, weather, seasons, locations, etc. from the collected training data.

The oxygen duration analyzer 134 may train one or more oxygen duration models 132 based on the extracted features (step 208). The oxygen duration analyzer 134 may train one or more oxygen duration models 132 based on an association of the one or more extracted features with associated durations of use left in one or more oxygen tanks 110. As previously mentioned, such extracted features may include user features such as age, heart rate, blood pressure, blood oxygen level, nervousness, pain, depression, hunger, sweating, etc. as well as tank usage features such as tank size, tank oxygen capacity, oxygen purity, date/time of tank changes, breaks in usage, weather, seasons, locations, etc., and the one or more oxygen duration models 132 may be generated through machine learning techniques such as convolutional neural networks. Moreover, the oxygen duration analyzer 134 may train the one or more oxygen duration models 132 to weight the features such that features shown to have a greater correlation with an accurate duration of use left in an oxygen tank 110 are weighted greater than those features that are not. Moreover, the oxygen duration analyzer 134 may train different oxygen duration models 132 for different users. In embodiments, the oxygen duration analyzer 134 may train a first oxygen duration model 132 to be used for all users, and subsequent oxygen duration models 132 personalized to different users after one or more iterations of determining a duration of use left in an oxygen tank 110. Based on the oxygen duration models 132's extracted features and weights associated with such extracted features, the oxygen duration analyzer 134 may later determine a duration of use left in an oxygen tank 110.

With reference to the previously introduced example where the oxygen duration analyzer 134 extracts user features such as age, heart rate, blood pressure, blood oxygen level, nervousness, pain, depression, hunger, sweating, etc. as well as tank usage features such as tank size, tank oxygen capacity, oxygen purity, date/time of tank changes, breaks in usage, weather, seasons, locations, etc. from the collected training data, the oxygen duration analyzer 134 trains a model for each identified user of the collected training data based on an association of the extracted features with the duration of use left in each oxygen tank 110 of the collected training data.

The oxygen duration analyzer 134 may receive a configuration (step 210). The oxygen duration analyzer 134 may receive a configuration by receiving a user registration and user preferences. The user registration may be uploaded by a user, i.e., a person using an oxygen tank 110, a person overseeing the usage of an oxygen tank 110 (caretaker, doctor, family member, etc.), etc. and the configuration may be received by the oxygen duration analyzer 134 via the oxygen duration client 122 and the network 108. Receiving the user registration may involve referencing a user profile via user login credentials, internet protocol (IP) address, media access control (MAC) address, etc., or receiving user input information such as a name, date of birth, address/geographic information, phone number, email address, company name, doctor's name, doctor's clinic address/geographic information, doctor's phone number, doctor's email address, device serial number, smart device 120 type, oxygen tank 110 type, types of the sensors 112, and the like. Lastly, the oxygen duration analyzer 134 may receive a configuration of the one or more sensors 112, whether they be fixed to one or more devices (e.g., the oxygen tank 110 and/or the smart device 120) or fixed within an environment in which the oxygen duration system 100 is implemented.

During configuration, the oxygen duration analyzer 134 may further receive user preferences (step 210 continued). User preferences may include preferences for the manner in which the oxygen duration analyzer 134 should notify one or more users and optionally others of a duration of use left in an oxygen tank 110. For example, a user may upload user preferences specifying that they are to be notified when the duration of use left in their oxygen tank 110 is less than or equal to one hour. In another example, a user may upload user preferences specifying that they are always to be notified of the duration of use left in their oxygen tank 110 on their smart device 120, and that their doctor is to be notified when the duration of use left in their oxygen tank 110 is equal to 72 hours, such that their doctor can prescribe and/or order a replacement oxygen tank 110 and the user can obtain the replacement oxygen tank 110 prior to the user's current oxygen tank 110 running out of oxygen.

With reference to the previously introduced example where the oxygen duration analyzer 134 trains a model for each identified user of the collected training data based on an association of the extracted features with the duration of use left in each oxygen tank 110 of the collected training data, the user uploads a user registration including the user's name, user's doctor's name and phone number, user's smartphone as smart device 120, and user's video cameras, heart rate monitor, blood pressure sensor, and oximeter sensor as sensors 112. The user also uploads user preferences specifying that notification of duration of use left in their oxygen tank 110 is to be communicated to the user via visual display on the user's smartphone smart device 120 when the duration is one hour or less.

The oxygen duration analyzer 134 may collect data (step 212). In embodiments, collected data may include data of the user, data of the user's oxygen tank 110, and data of the oxygen tank usage conditions. The oxygen duration analyzer 134 may collect data via user upload/input, databases, or the sensors 112. In embodiments, the oxygen duration analyzer 134 may collect data via the sensors 112 as one or more microphones built into an auditorium, a camera built into a facility, a heart rate monitor worn by a user, etc. For example, heart rate monitor and blood pressure sensors 112 may collect the user's heart rate and blood pressure. The collected data may additionally include user demographics from one or more databases and user input specifying when the user is stressed and hungry (while using their oxygen tank 110). The oxygen duration analyzer 134 may collect data to later extract features of the collected data and apply one or more oxygen duration models 132 to determine a duration of use left in the user's oxygen tank 110.

With reference to the previously introduced example where the user uploads a user registration and user preferences, the oxygen duration analyzer 134 collects data of the user, data of the user's oxygen tank 110, and data of the oxygen tank usage conditions.

The oxygen duration analyzer 134 may extract one or more features from the collected data (step 214). The oxygen duration analyzer 134 may extract one or more features from the collected data in the same manner as described above with respect to extracting features from the training data. However, the oxygen duration analyzer 134 extracts one or more features from the current collected data instead of from the previously collected training data.

With reference to the previously introduced example where the oxygen duration analyzer 134 collects data of the user, data of the user's oxygen tank 110, and data of the oxygen tank usage conditions, the oxygen duration analyzer 134 extracts the features listed in Table 1 below.

TABLE 1

Extracted Features

| | |
|---|---|
| Age | 45 |
| Heart Rate | 80 beats per minute |
| Blood Pressure | 120/80 mmHg |
| Blood Oxygen Level | 90 mmHg |
| Nervousness | None |
| Pain | Minimal |
| Depression | None |
| Hunger | None |
| Sweating | Minimal |
| Tank size | E Cylinder (approx. length of 25") |
| Tank oxygen Capacity | 660 Liters |
| Date/Time of Oxygen Tank 110 Change | May 3, 2020 at 9:30 AM |
| Breaks in Usage | None |
| Weather | 70 degrees Fahrenheit |
| Season | Spring |

The oxygen duration analyzer 134 may apply one or more models to the extracted features to determine a duration of use left in an oxygen tank 110 (step 216). As previously mentioned, such extracted features may include user features such as age, heart rate, blood pressure, blood oxygen level, nervousness, pain, depression, hunger, sweating, etc. as well as tank usage features such as tank size, tank oxygen capacity, oxygen purity, date/time of tank changes, breaks in usage, weather, seasons, locations, etc., and the one or more oxygen duration models 132 may be generated through machine learning techniques such as neural networks. In embodiments, the one or more oxygen duration models 132 may be trained at initialization and/or through the use of a feedback loop to weight the features such that features shown to have a greater correlation with determining an accurate duration of use left in an oxygen tank 110 are weighted greater than those features that are not. Based on the extracted features and weights associated with such extracted features, the oxygen duration analyzer 134 may determine a duration of use left in an oxygen tank 110. In some embodiments, the oxygen duration analyzer 134 may determine a range of duration of use left in an oxygen tank 110. For example, the oxygen duration analyzer 134 may determine that a user's oxygen tank 110 has between 7 minutes and 9 minutes of usage remaining. In embodiments, the oxygen duration analyzer 134 may additionally or alternatively determine an average rate of oxygen consumption, average duration of time per oxygen tank 110 for the user, etc. in order to later modify one or more oxygen duration models 132 and/or provide one or more doctors, researchers, professionals, etc. with data to be used for technological advancements and/or developments. In embodiments where multiple oxygen duration models 132 are trained for various individuals but no oxygen duration models 132 is trained for the particular user, the oxygen duration analyzer 134 may apply an oxygen duration model 132 of a different individual with similar demographics and/or characteristics as the user.

With reference to the previously introduced example where the oxygen duration analyzer 134 extracts features from the collected data, the oxygen duration analyzer 134 applies the previously trained model for the user to determine that the user's oxygen tank 110 will last for 30 more minutes.

Upon the oxygen duration analyzer 134 determining a duration of use left in the user's oxygen tank 110, the oxygen duration analyzer 134 may notify the user and/or others of the duration (step 218). The oxygen duration analyzer 134 may notify the user and/or others in the form of audio, video, text, or any other manner via the smart device 120 or any other device. The notification may be conveyed visually via text and/or audially via one or more integrated speakers. In embodiments, the oxygen duration analyzer 134 may notify one or more of the user's doctors of the duration of use left in the user's oxygen tank 110 such that the doctor may make one or more prescriptions based on the duration of use left. In embodiments, the oxygen duration analyzer 134 may notify a parent of a user of the duration of use left in the user's oxygen tank 110 (i.e., if the parent oversees the user's health). In embodiments, the oxygen duration analyzer 134 may notify one or more administrators such as researchers, professionals, etc. of the duration of use left in the user's oxygen tank 110. In embodiments, the oxygen duration analyzer 134 may notify the user and/or one or more administrators when the determined duration of use left in the user's oxygen tank crosses below a threshold. In embodiments, the oxygen duration analyzer 134 may determine an appropriate threshold based on the user's distance or time of travel away from a new oxygen tank (i.e., determined from collected GPS data). For example, if the user is approximately 45 minutes away from a new oxygen tank located at the user's house, the oxygen duration analyzer 134 may notify the user when the duration of use of their oxygen tank 110 crosses below 50 minutes. As previously discussed, the oxygen duration analyzer 134 may notify the user and/or others of the duration of use left in the user's oxygen tank 110 according to the user preferences of configuration.

With reference to the previously introduced example where the oxygen duration analyzer 134 determines that the user's oxygen tank 110 will last for 30 more minutes, the oxygen duration analyzer 134 visually notifies the user that their oxygen tank 110 will last for 30 more minutes on the user's smart device 120 according to the user's preferences.

The oxygen duration analyzer 134 may evaluate and modify the oxygen duration models 132 (step 220). In the example embodiment, the oxygen duration analyzer 134 may verify whether the duration of use left in the user's oxygen tank 110 was accurate in order to provide a feedback loop for modifying the oxygen duration models 132. In embodiments, the feedback loop may simply provide a means for a user to indicate whether the determined duration of use left seemed accurate, helpful, etc. The feedback loop indication may be triggered via a toggle switch, button, slider, etc. that may be selected by the user manually by hand using a button/touchscreen/etc., by voice, by eye movement, and the like. Based on the oxygen duration analyzer 134 accurately or inaccurately determining a duration of use left in the user's oxygen tank 110, the oxygen duration analyzer 134 may modify the oxygen duration models 132 relating to determination of a duration of use left in an oxygen tank 110. In other embodiments, the oxygen duration analyzer 134 may infer or deduce whether the determined duration of use left was accurate. For example, the oxygen duration analyzer 134 may interpret user dialogue via natural language processing to determine whether the determination was accurate. For example, if the user says, "I thought I had 30 minutes" or other expressions indicative of confusion or dissatisfaction, the oxygen duration analyzer 134 may infer that the determination was inaccurate because it overestimated a duration of use left, and modify the oxygen duration models 132 accordingly. In another example, if the user says, "This lasted longer than expected" or other expressions indicative of being pleasantly surprised, the oxygen duration analyzer 134 may infer that the determination was inaccurate because it underestimated a duration of use left, and modify the oxygen duration models 132 accordingly. In a third example, if a user proceeds to change their tank 110 earlier or later than expected based on the determined duration of use left, the oxygen duration analyzer 134 may infer that the determined duration of use left was inaccurate and modify the oxygen duration models 132 accordingly. Based on feedback received in the above or any other manners, the oxygen duration analyzer 134 may then modify the oxygen duration models 132 to more accurately determine a duration of use left in an oxygen tank 110.

With reference to the previously introduced example where the oxygen duration analyzer 134 visually notifies the user that their oxygen tank 110 will last for 30 more minutes on the user's smart device 120 according to the user's preferences, the user says, "I thought I only had 30 minutes" as they change their oxygen tank 110 35 minutes after the determination. The oxygen duration analyzer 134 modifies the oxygen duration models 132 accordingly.

Figure 3:
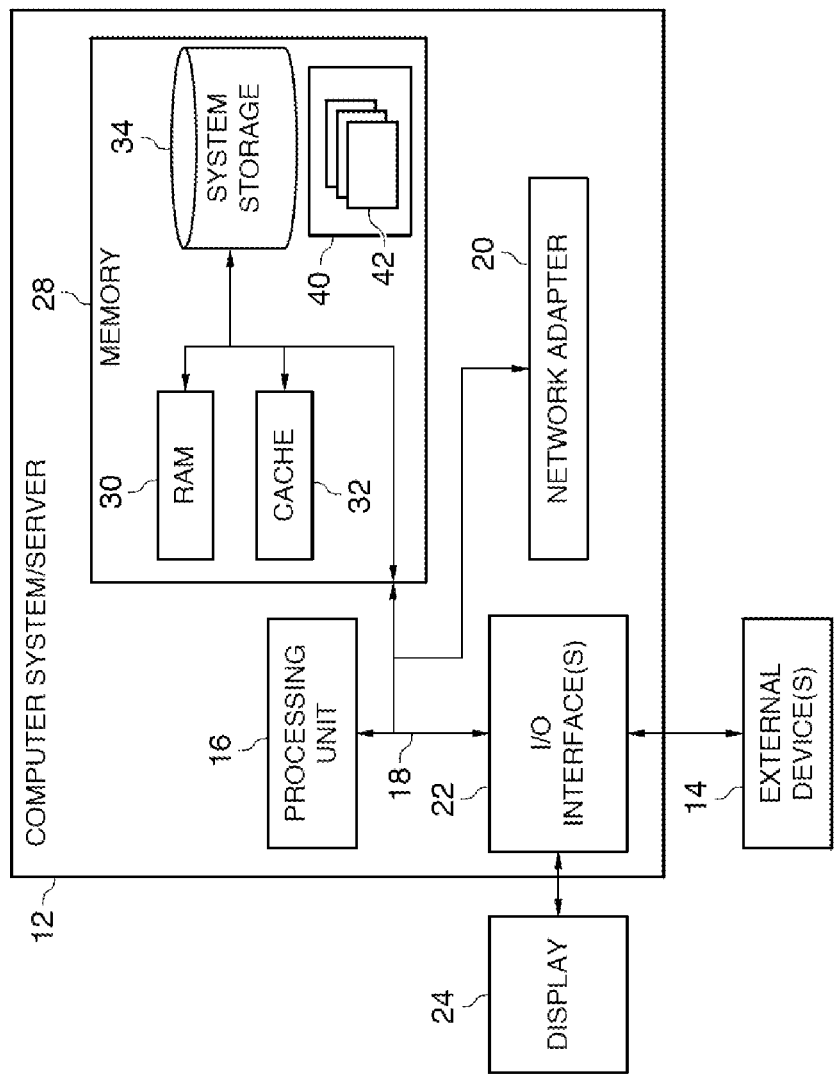
FIG. 3 depicts an exemplary block diagram depicting the hardware components of the oxygen duration system 100 of FIG. 1, in accordance with the exemplary embodiments.

FIG. 3 depicts a block diagram of devices within the oxygen duration system 100 of FIG. 1, in accordance with the exemplary embodiments. It should be appreciated that FIG. 3 provides only an illustration of one implementation and does not imply any limitations with regard to the environments in which different embodiments may be implemented. Many modifications to the depicted environment may be made.

Devices used herein may include one or more processors 02, one or more computer-readable RAMs 04, one or more computer-readable ROMs 06, one or more computer readable storage media 08, device drivers 12, read/write drive or interface 14, network adapter or interface 16, all interconnected over a communications fabric 18. Communications fabric 18 may be implemented with any architecture designed for passing data and/or control information between processors (such as microprocessors, communications and network processors, etc.), system memory, peripheral devices, and any other hardware components within a system.

One or more operating systems 10, and one or more application programs 11 are stored on one or more of the computer readable storage media 08 for execution by one or more of the processors 02 via one or more of the respective RAMs 04 (which typically include cache memory). In the illustrated embodiment, each of the computer readable storage media 08 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Devices used herein may also include a RAY drive or interface 14 to read from and write to one or more portable computer readable storage media 26. Application programs 11 on said devices may be stored on one or more of the portable computer readable storage media 26, read via the respective R/W drive or interface 14 and loaded into the respective computer readable storage media 08.

Devices used herein may also include a network adapter or interface 16, such as a TCP/IP adapter card or wireless communication adapter (such as a 4G wireless communication adapter using OFDMA technology). Application programs 11 on said computing devices may be downloaded to the computing device from an external computer or external storage device via a network (for example, the Internet, a local area network or other wide area network or wireless network) and network adapter or interface 16. From the network adapter or interface 16, the programs may be loaded onto computer readable storage media 08. The network may comprise copper wires, optical fibers, wireless transmission, routers, firewalls, switches, gateway computers and/or edge servers.

Devices used herein may also include a display screen 20, a keyboard or keypad 22, and a computer mouse or touchpad 24. Device drivers 12 interface to display screen 20 for imaging, to keyboard or keypad 22, to computer mouse or touchpad 24, and/or to display screen 20 for pressure sensing of alphanumeric character entry and user selections. The device drivers 12, RAY drive or interface 14 and network adapter or interface 16 may comprise hardware and software (stored on computer readable storage media 08 and/or ROM 06).

The programs described herein are identified based upon the application for which they are implemented in a specific one of the exemplary embodiments. However, it should be appreciated that any particular program nomenclature herein is used merely for convenience, and thus the exemplary embodiments should not be limited to use solely in any specific application identified and/or implied by such nomenclature.

Based on the foregoing, a computer system, method, and computer program product have been disclosed. However, numerous modifications and substitutions can be made without deviating from the scope of the exemplary embodiments. Therefore, the exemplary embodiments have been disclosed by way of example and not limitation.

It is to be understood that although this disclosure includes a detailed description on cloud computing, implementation of the teachings recited herein are not limited to a cloud computing environment. Rather, the exemplary embodiments are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or data center).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
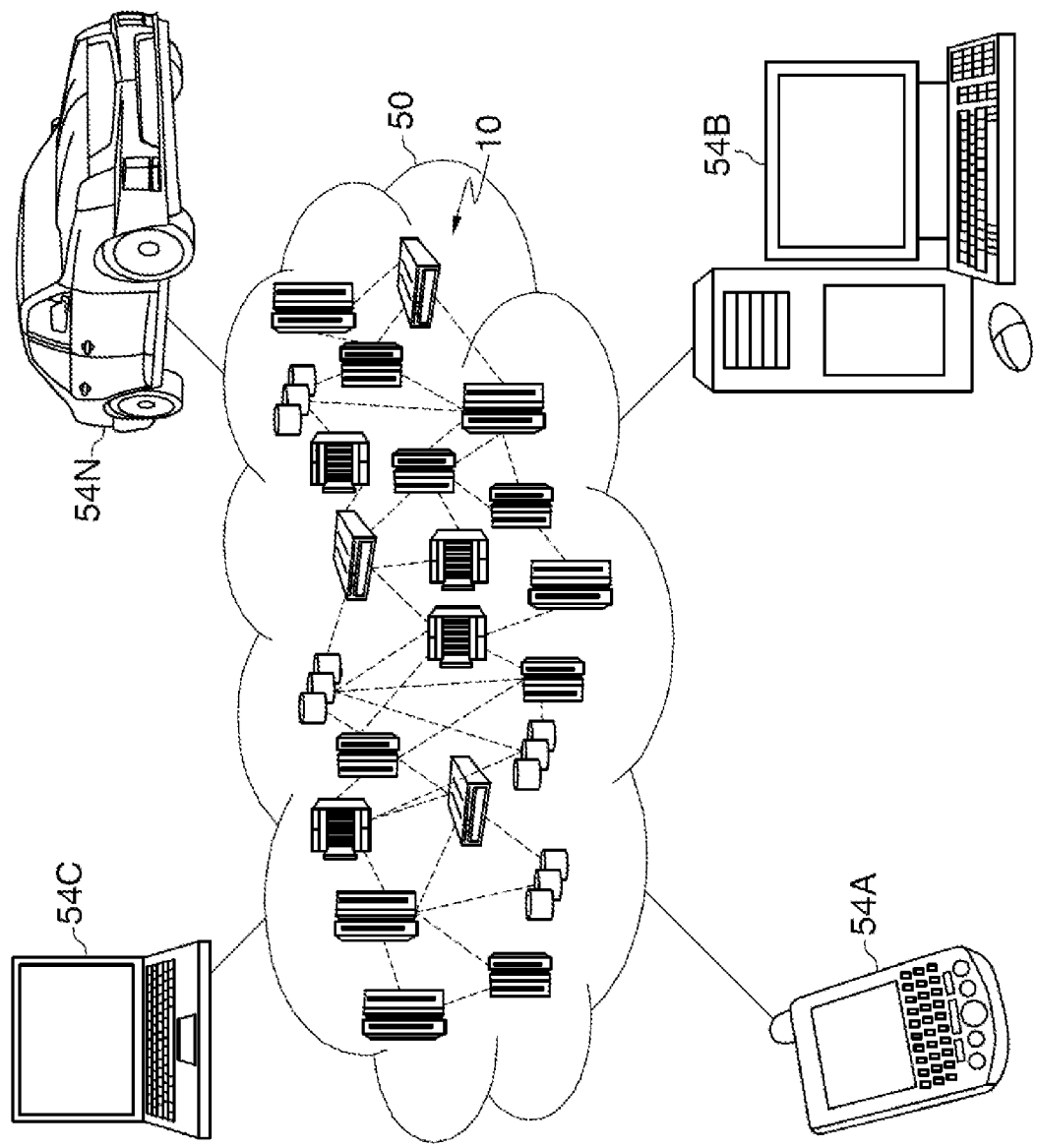
FIG. 4 depicts a cloud computing environment, in accordance with the exemplary embodiments.

Referring now to FIG. 4, illustrative cloud computing environment 50 is depicted. As shown, cloud computing environment 50 includes one or more cloud computing nodes 40 with which local computing devices used by cloud consumers, such as, for example, personal digital assistant (PDA) or cellular telephone 54A, desktop computer 54B, laptop computer 54C, and/or automobile computer system 54N may communicate. Nodes 40 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 40 and cloud computing environment 50 can communicate with any type of computerized device over any type of network and/or network addressable connection (e.g., using a web browser).

Figure 5:
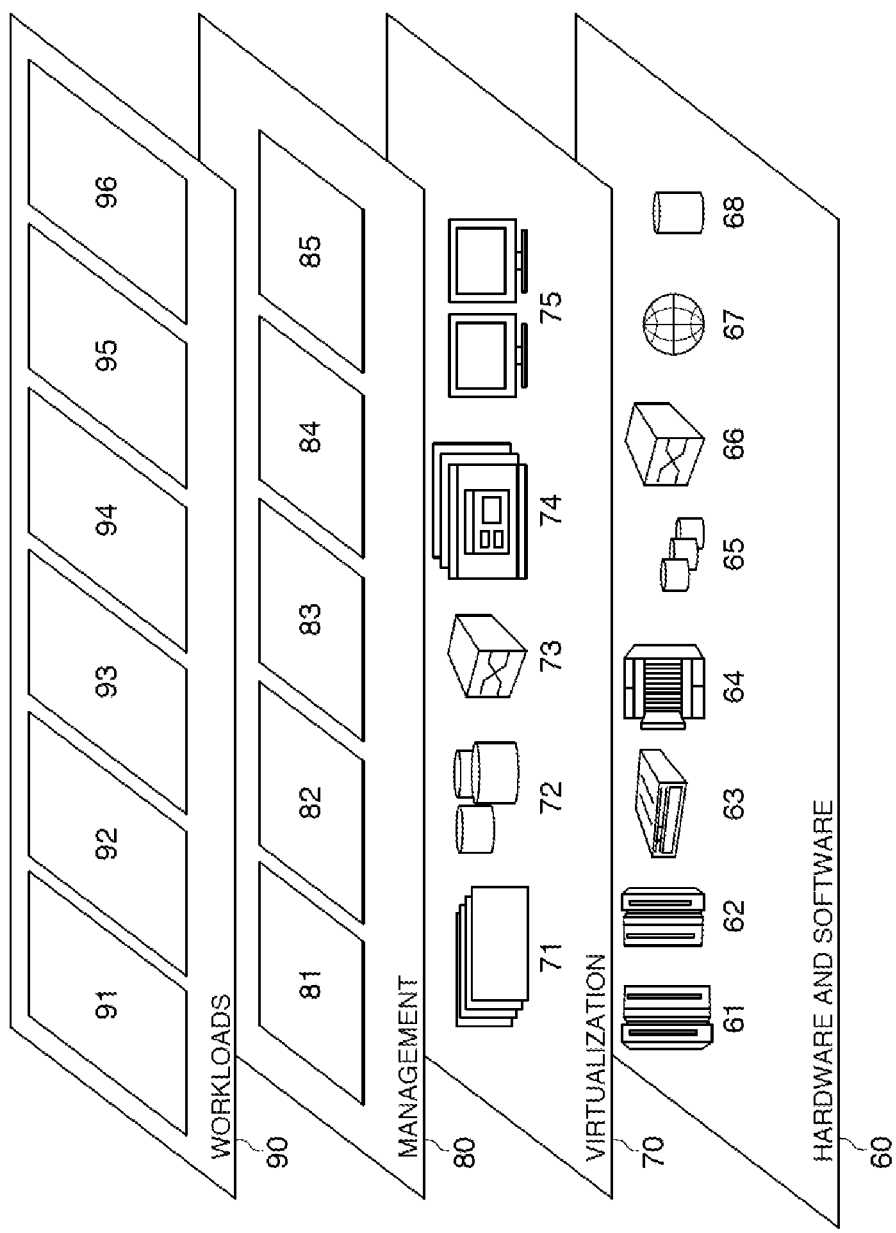
FIG. 5 depicts abstraction model layers, in accordance with the exemplary embodiments.

Referring now to FIG. 5, a set of functional abstraction layers provided by cloud computing environment 50 (FIG. 4) is shown. It should be understood in advance that the components, layers, and functions shown in FIG. 5 are intended to be illustrative only and the exemplary embodiments are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and oxygen tank duration determination 96.

The exemplary embodiments may be a system, a method, and/or a computer program product at any possible technical detail level of integration. The computer program product may include a computer readable storage medium (or media) having computer readable program instructions thereon for causing a processor to carry out aspects of the exemplary embodiments.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the exemplary embodiments may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the exemplary embodiments.

Aspects of the exemplary embodiments are described herein with reference to flowchart illustrations and/or block diagrams of methods, apparatus (systems), and computer program products according to the exemplary embodiments. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various exemplary embodiments. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for determining a duration of use left in an oxygen tank, the method comprising:
    collecting data of a user and corresponding oxygen tank;
    extracting one or more features from the collected data; and
    determining a duration of use left in the oxygen tank based on the extracted one or more features and one or more models, wherein the one or more models are previously trained at least in part using training features extracted from training data of the user.

2. The method of claim 1, further comprising:
    notifying the user and one or more administrators of the duration of use left in the oxygen tank.

3. The method of claim 1, further comprising:
    notifying the user when the duration of use is lower than a threshold, wherein the threshold is determined based on a distance of the user and/or time of travel away from a new oxygen tank.

4. The method of claim 1, wherein the one or more models correlate the one or more features with the likelihood of accurately determining a duration of use left in the oxygen tank.

5. The method of claim 1, further comprising:
    receiving feedback indicative of whether the duration of use left in the oxygen tank is accurate; and
    adjusting the one or more models based on the received feedback.

6. The method of claim 1, further comprising:
    collecting the training data of the user, wherein the training data is collected from a source selected from the group consisting of: an upload from the user, input from the user, a database having information about the user, one or more sensors worn by the user, and one or more sensors for collecting data in a vicinity of the user;
    extracting the training features from the training data; and
    training the one or more models based on the extracted training features.

7. The method of claim 1, wherein the one or more features include one or more features selected from the group consisting of: age, heart rate, blood pressure, blood oxygen level, nervousness, pain, depression, hunger, sweating, tank size, tank oxygen capacity, oxygen purity, date of tank changes, time of tank changes, breaks in usage, weather, seasons, and locations.

8. A computer program product for determining a duration of use left in an oxygen tank, the computer program product comprising:
    one or more non-transitory computer-readable storage media and program instructions stored on the one or more non-transitory computer-readable storage media capable of performing a method, the method comprising:
    collecting data of a user and corresponding oxygen tank;
    extracting one or more features from the collected data;
    determining a duration of use left in the oxygen tank based on the extracted one or more features and one or more models;
    receiving feedback indicative of whether the duration of use left in the oxygen tank is accurate; and
    adjusting the one or more models based on the received feedback.

9. The computer program product of claim 8, further comprising:
    notifying the user and one or more administrators of the duration of use left in the oxygen tank.

10. The computer program product of claim 8, further comprising:
    notifying the user when the duration of use is lower than a threshold, wherein the threshold is determined based on a distance of the user and/or time of travel away from a new oxygen tank.

11. The computer program product of claim 8, wherein the one or more models correlate the one or more features with the likelihood of accurately determining a duration of use left in the oxygen tank.

12. The computer program product of claim 8, wherein the feedback indicative of whether the duration of use left in the oxygen tank is accurate is received from the user and/or is based on user activity; and comprising adjusting the one or more models based on the feedback.

13. The computer program product of claim 8, further comprising:
    collecting training data;
    extracting training features from the training data; and
    training the one or more models based on the extracted training features.

14. The computer program product of claim 8, wherein the one or more features include one or more features selected from the group consisting of: age, heart rate, blood pressure, blood oxygen level, nervousness, pain, depression, hunger, sweating, tank size, tank oxygen capacity, oxygen purity, date of tank changes, time of tank changes, breaks in usage, weather, seasons, and locations.

15. A computer system for determining a duration of use left in an oxygen tank, the computer system comprising:
    one or more computer processors, one or more computer-readable storage media, and program instructions stored on the one or more of the computer-readable storage media for execution by at least one of the one or more processors capable of performing a method, the method comprising:
    collecting data of a user and corresponding oxygen tank;
    extracting one or more features from the collected data;
    determining a duration of use left in the oxygen tank based on the extracted one or more features and one or more models; and notifying the user when the duration of use is lower than a threshold, wherein the threshold is determined based at least in part on a location of the user.

16. The computer system of claim 15, further comprising: notifying the user and one or more administrators of the duration of use left in the oxygen tank.

17. The computer system of claim 15, further comprising: wherein the threshold is determined based on a distance of the user and/or time of travel away from a new oxygen tank.

18. The computer system of claim 15, wherein the one or more models correlate the one or more features with the likelihood of accurately determining a duration of use left in the oxygen tank.

19. The computer system of claim 15, further comprising: receiving feedback indicative of whether the duration of use left in the oxygen tank is accurate; and
adjusting the one or more models based on the received feedback.

20. The computer system of claim 15, further comprising: collecting training data;
extracting training features from the training data; and
training the one or more models based on the extracted training features.

* * * * *